(12) United States Patent
Li et al.

(10) Patent No.: US 10,537,730 B2
(45) Date of Patent: Jan. 21, 2020

(54) CONTINUOUS CONDUCTIVE MATERIALS FOR ELECTROMAGNETIC SHIELDING

(75) Inventors: Bernard Li, Plymouth, MN (US); Chad Cai, Woodbury, MN (US); Xingfu Chen, Eden Prairie, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 1696 days.

(21) Appl. No.: 11/674,995

(22) Filed: Feb. 14, 2007

(65) Prior Publication Data
US 2008/0195186 A1    Aug. 14, 2008

(51) Int. Cl.
*A61N 1/04* (2006.01)
*A61N 1/05* (2006.01)
*A61N 1/37* (2006.01)

(52) U.S. Cl.
CPC ......... *A61N 1/0551* (2013.01); *A61N 1/3718* (2013.01)

(58) Field of Classification Search
CPC ................ A61N 1/3718; A61N 2001/086
USPC .................... 607/2, 9, 36, 115, 116
See application file for complete search history.

(56) References Cited

U.S. PATENT DOCUMENTS

| | | |
|---|---|---|
| 3,788,329 A | 1/1974 | Friedman |
| 3,915,174 A | 10/1975 | Preston |
| 4,038,990 A | 8/1977 | Thompson |
| 4,220,813 A | 9/1980 | Kyle |
| 4,280,507 A | 7/1981 | Rosenberg |
| 4,320,763 A | 3/1982 | Money |
| 4,383,225 A | 5/1983 | Mayer |
| 4,628,942 A | 12/1986 | Sweeney et al. |
| 4,711,027 A | 12/1987 | Harris |

(Continued)

FOREIGN PATENT DOCUMENTS

| | | |
|---|---|---|
| EP | 0624383 | 11/1994 |
| EP | 0713714 | 5/1996 |

(Continued)

OTHER PUBLICATIONS

Chung, D.D.L., Electromagnetic interference shielding effectiveness of carbon materials, Carbon 29 (2001), pp. 279-285, 2001 Elsevier Science Ltd.

(Continued)

*Primary Examiner* — Michael J D Abreu
(74) *Attorney, Agent, or Firm* — Withers & Keys, LLC

(57) ABSTRACT

A medical electrical lead having a conductor assembly covered by an insulating layer, and a shield covering positioned adjacent or proximate to at least a portion of the insulating layer in order to shield the conductor assembly from one or more electromagnetic fields. The shield covering is formed of a material that is electrically conductive, where the material is in a wrapped or woven form. The material is selected so as to have an effective combination of small size and high conductive surface area, e.g., as opposed to metal wire or coatings thinner than metal wire. As such, the shield covering exhibits sufficient conductivity in the presence of one or more high frequency electromagnetic fields so that interference to the operation of the conductor assembly is minimized. The material can have a coating formed of one or more metals. The material can include carbon. In turn, the carbon can be formed of one or more of carbon fiber, carbon nanofiber, and single or multi-walled carbon nanotube.

13 Claims, 10 Drawing Sheets

(56) References Cited

U.S. PATENT DOCUMENTS

| | | | |
|---|---|---|---|
| 4,726,379 A | 2/1988 | Altman et al. | |
| 4,852,585 A | 8/1989 | Heath | |
| 4,920,980 A | 5/1990 | Jackowski | |
| 4,947,866 A | 8/1990 | Lessar et al. | |
| 4,951,672 A | 8/1990 | Buchwald et al. | |
| 4,991,583 A | 2/1991 | Silvian | |
| 5,012,045 A | 4/1991 | Sato | |
| 5,018,523 A | 5/1991 | Bach, Jr. et al. | |
| 5,020,544 A | 6/1991 | Dahl et al. | |
| 5,020,545 A | 6/1991 | Soukup | |
| 5,036,862 A | 8/1991 | Pohndorf | |
| 5,040,544 A | 8/1991 | Lessar et al. | |
| 5,063,932 A | 11/1991 | Dahl et al. | |
| 5,197,468 A | 3/1993 | Proctor et al. | |
| 5,217,010 A | 6/1993 | Tsitlik et al. | |
| 5,246,438 A | 9/1993 | Langberg | |
| 5,260,128 A | 11/1993 | Ishii et al. | |
| 5,271,417 A | 12/1993 | Swanson et al. | |
| 5,314,459 A | 5/1994 | Swanson et al. | |
| 5,323,776 A | 6/1994 | Blakely et al. | |
| 5,335,657 A | 8/1994 | Terry, Jr. et al. | |
| 5,349,133 A | 9/1994 | Rogers | |
| 5,366,496 A | 11/1994 | Dahl et al. | |
| 5,370,644 A | 12/1994 | Langberg | |
| 5,374,778 A | 12/1994 | Hashimoto et al. | |
| 5,417,719 A | 5/1995 | Hull et al. | |
| 5,458,629 A | 10/1995 | Baudino et al. | |
| 5,466,252 A | 11/1995 | Soukup et al. | |
| 5,476,496 A | 12/1995 | Strandberg et al. | |
| 5,504,274 A | 4/1996 | McCabe et al. | |
| 5,514,172 A | 5/1996 | Mueller | |
| 5,515,848 A | 5/1996 | Corbett, III et al. | |
| 5,523,578 A | 6/1996 | Herskovic | |
| 5,527,348 A | 6/1996 | Winkler et al. | |
| 5,591,218 A | 1/1997 | Jacobson | |
| 5,594,304 A | 1/1997 | Graber | |
| 5,609,622 A | 3/1997 | Soukup et al. | |
| 5,629,622 A | 5/1997 | Scampini | |
| 5,649,965 A | 7/1997 | Pons et al. | |
| 5,662,697 A | 9/1997 | Li et al. | |
| 5,676,694 A | 10/1997 | Boser et al. | |
| 5,683,435 A | 11/1997 | Truex et al. | |
| 5,697,909 A | 12/1997 | Eggers et al. | |
| 5,697,958 A | 12/1997 | Paul et al. | |
| 5,702,437 A | 12/1997 | Baudino | |
| 5,722,998 A | 3/1998 | Prutchi et al. | |
| 5,727,552 A | 3/1998 | Ryan | |
| 5,751,539 A | 5/1998 | Stevenson et al. | |
| 5,782,241 A | 7/1998 | Felblinger et al. | |
| 5,814,076 A | 9/1998 | Brownlee | |
| 5,827,997 A * | 10/1998 | Chung et al. | 174/388 |
| 5,830,136 A | 11/1998 | Delonzor et al. | |
| 5,851,226 A | 12/1998 | Skubitz et al. | |
| 5,905,627 A | 5/1999 | Brendel et al. | |
| 5,927,345 A | 7/1999 | Sampson | |
| 5,954,760 A | 9/1999 | Jarl | |
| 5,964,705 A | 10/1999 | Truwit et al. | |
| 5,970,429 A | 10/1999 | Martin | |
| 5,942,966 A | 12/1999 | Markoll | |
| 6,033,408 A | 3/2000 | Gage et al. | |
| 6,055,457 A | 4/2000 | Bonner | |
| 6,101,417 A | 8/2000 | Vogel et al. | |
| 6,195,267 B1 | 2/2001 | MacDonald et al. | |
| 6,198,972 B1 | 3/2001 | Hartlaub et al. | |
| 6,209,764 B1 | 4/2001 | Hartlaub et al. | |
| 6,258,071 B1 | 7/2001 | Brookes | |
| 6,265,466 B1 | 7/2001 | Glatkowski | |
| 6,284,971 B1 | 9/2001 | Atalar et al. | |
| 6,302,740 B1 | 10/2001 | Holmstrom | |
| 6,348,070 B1 | 2/2002 | Teissl et al. | |
| 6,424,234 B1 | 7/2002 | Stevenson | |
| 6,471,699 B1 | 10/2002 | Fleischman et al. | |
| 6,488,704 B1 | 12/2002 | Connelly et al. | |
| 6,494,916 B1 | 12/2002 | Babalola et al. | |
| 6,501,991 B1 | 12/2002 | Honeck et al. | |
| 6,503,648 B1 | 1/2003 | Wang | |
| 6,506,972 B1 | 1/2003 | Wang | |
| 6,529,774 B1 | 3/2003 | Greene | |
| 6,538,191 B1 | 3/2003 | MacDonald | |
| 6,606,521 B2 | 8/2003 | Paspa et al. | |
| 6,640,137 B2 | 10/2003 | MacDonald | |
| 6,660,116 B2 | 12/2003 | Wolf et al. | |
| 6,671,544 B2 | 12/2003 | Baudino et al. | |
| 6,673,999 B1 * | 1/2004 | Wang | B82Y 25/00 174/36 |
| 6,675,033 B1 | 1/2004 | Lardo et al. | |
| 6,695,761 B2 | 2/2004 | Oschman et al. | |
| 6,708,051 B1 | 3/2004 | Durousseau | |
| 6,711,440 B2 | 3/2004 | Deal et al. | |
| 6,712,844 B2 | 3/2004 | Pacetti et al. | |
| 6,713,671 B1 | 3/2004 | Wang et al. | |
| 6,718,203 B2 | 4/2004 | Weiner et al. | |
| 6,718,207 B2 | 4/2004 | Connelly | |
| 6,725,092 B2 | 4/2004 | MacDonald et al. | |
| 6,735,471 B2 | 5/2004 | Hill et al. | |
| 6,741,892 B1 | 5/2004 | Meadows et al. | |
| 6,750,055 B1 | 6/2004 | Connelly et al. | |
| 6,757,566 B2 | 6/2004 | Weiner et al. | |
| 6,760,628 B2 | 7/2004 | Weiner et al. | |
| 6,763,268 B2 | 7/2004 | MacDonald et al. | |
| 6,765,144 B1 | 7/2004 | Wang et al. | |
| 6,768,053 B1 | 7/2004 | Wang et al. | |
| 6,778,856 B2 | 8/2004 | Connelly et al. | |
| 6,785,736 B1 | 9/2004 | Connelly et al. | |
| 6,792,316 B2 | 9/2004 | Sass | |
| 6,793,642 B2 | 9/2004 | Connelly et al. | |
| 6,795,730 B2 | 9/2004 | Connelly et al. | |
| 6,795,736 B2 | 9/2004 | Connelly et al. | |
| 6,799,067 B2 | 9/2004 | Pacetti | |
| 6,799,069 B2 | 9/2004 | Weiner et al. | |
| 6,815,609 B1 | 11/2004 | Wang et al. | |
| 6,819,954 B2 | 11/2004 | Connelly | |
| 6,819,958 B2 | 11/2004 | Weiner et al. | |
| 6,844,492 B1 | 1/2005 | Wang et al. | |
| 6,845,259 B2 | 1/2005 | Pacetti et al. | |
| 6,845,267 B2 | 1/2005 | Harrison et al. | |
| 6,850,805 B2 | 2/2005 | Connelly et al. | |
| 6,852,091 B2 | 2/2005 | Edwards et al. | |
| 6,864,418 B2 | 3/2005 | Wang et al. | |
| 6,869,683 B2 | 3/2005 | Sakurai et al. | |
| 6,871,091 B2 | 3/2005 | Wilkinson et al. | |
| 6,872,882 B2 | 3/2005 | Fritz | |
| 6,875,180 B2 | 4/2005 | Weiner et al. | |
| 6,879,861 B2 | 4/2005 | Benz et al. | |
| 6,882,519 B2 | 4/2005 | Uzawa et al. | |
| 6,895,280 B2 | 5/2005 | Meadows et al. | |
| 6,901,290 B2 | 5/2005 | Foster et al. | |
| 6,906,256 B1 | 6/2005 | Wang | |
| 6,920,361 B2 | 7/2005 | Williams | |
| 6,922,590 B1 | 7/2005 | Whitehurst | |
| 6,925,328 B2 | 8/2005 | Foster et al. | |
| 6,930,242 B1 | 8/2005 | Helfer | |
| 6,937,906 B2 | 8/2005 | Terry et al. | |
| 6,944,489 B2 | 9/2005 | Zeiljemaker et al. | |
| 6,949,929 B2 | 9/2005 | Gray et al. | |
| 6,954,674 B2 | 10/2005 | Connelly | |
| 6,968,236 B2 | 11/2005 | Hagele | |
| 6,971,391 B1 | 12/2005 | Wang et al. | |
| 6,980,865 B1 | 12/2005 | Wang et al. | |
| 6,982,378 B2 | 1/2006 | Dickson | |
| 6,985,775 B2 | 1/2006 | Reinke et al. | |
| 6,993,387 B2 | 1/2006 | Connelly et al. | |
| 6,999,818 B2 | 2/2006 | Stevenson et al. | |
| 6,999,821 B2 | 2/2006 | Jenney et al. | |
| 7,013,174 B2 | 3/2006 | Connelly et al. | |
| 7,013,180 B2 | 3/2006 | Villaseca et al. | |
| 7,015,393 B2 | 3/2006 | Weiner | |
| 7,050,855 B2 | 5/2006 | Zeiljemaker et al. | |
| 7,076,283 B2 | 7/2006 | Cho et al. | |
| 7,082,328 B2 | 7/2006 | Funke | |
| 7,103,413 B2 | 9/2006 | Swanson | |
| 7,123,013 B2 | 10/2006 | Gray | |
| 7,174,219 B2 | 2/2007 | Wahlstrand et al. | |
| 7,233,825 B2 | 6/2007 | Jorgenson et al. | |

(56) References Cited

U.S. PATENT DOCUMENTS

| | | | |
|---|---|---|---|
| 7,257,449 | B2 | 8/2007 | Bodner |
| 7,292,894 | B2 | 11/2007 | Belden |
| 7,319,901 | B2 | 1/2008 | Dublin |
| 7,363,090 | B2 | 4/2008 | Halperin |
| 7,389,148 | B1 | 6/2008 | Morgan |
| 2002/0116028 | A1 | 8/2002 | Greatbatch et al. |
| 2002/0116029 | A1 | 8/2002 | Miller et al. |
| 2002/0116033 | A1 | 8/2002 | Greatbatch et al. |
| 2002/0116034 | A1 | 8/2002 | Miller et al. |
| 2002/0133202 | A1 | 9/2002 | Connelly et al. |
| 2002/0138110 | A1 | 9/2002 | Connelly et al. |
| 2002/0183438 | A1 | 12/2002 | Amarasekera et al. |
| 2003/0093107 | A1 | 5/2003 | Parsonage et al. |
| 2003/0109901 | A1 | 6/2003 | Greatbatch |
| 2003/0117787 | A1 | 6/2003 | Nakauchi |
| 2003/0120197 | A1 | 6/2003 | Kaneko et al. |
| 2003/0144718 | A1 | 7/2003 | Zeijlemaker |
| 2003/0144719 | A1 | 7/2003 | Zeijlemaker |
| 2003/0144720 | A1 | 7/2003 | Villaseca et al. |
| 2003/0204217 | A1 | 10/2003 | Greatbatch |
| 2003/0225331 | A1 | 12/2003 | Diederich et al. |
| 2004/0020674 | A1 | 2/2004 | Fadden et al. |
| 2004/0028859 | A1 | 2/2004 | LeGrande et al. |
| 2004/0068307 | A1 | 4/2004 | Goble |
| 2004/0071949 | A1 | 4/2004 | Glatkowski et al. |
| 2004/0199069 | A1* | 10/2004 | Connelly et al. ............. 600/412 |
| 2004/0249428 | A1 | 12/2004 | Wang et al. |
| 2004/0263174 | A1 | 12/2004 | Gray et al. |
| 2005/0065587 | A1 | 3/2005 | Gryzwa |
| 2005/0070972 | A1 | 3/2005 | Wahlstrand |
| 2005/0080471 | A1 | 4/2005 | Chitre et al. |
| 2005/0113876 | A1 | 5/2005 | Weiner et al. |
| 2005/0159661 | A1 | 7/2005 | Connelly et al. |
| 2005/0182471 | A1 | 8/2005 | Wang |
| 2005/0222642 | A1 | 10/2005 | Przybyszewski |
| 2005/0222656 | A1 | 10/2005 | Wahlstrand |
| 2005/0222657 | A1 | 10/2005 | Wahlstrand |
| 2005/0222658 | A1 | 10/2005 | Hoegh |
| 2005/0222659 | A1 | 10/2005 | Olsen |
| 2006/0155270 | A1 | 7/2006 | Hancock |
| 2006/0200218 | A1 | 9/2006 | Wahlstrand |
| 2006/0247747 | A1 | 11/2006 | Olsen |
| 2006/0247748 | A1 | 11/2006 | Wahlstrand |
| 2007/0106332 | A1 | 5/2007 | Denker |
| 2007/0185556 | A1 | 8/2007 | Williams |
| 2008/0033497 | A1 | 2/2008 | Bulkes |
| 2008/0039709 | A1 | 2/2008 | Karmarkar |
| 2008/0195187 | A1 | 8/2008 | Li |
| 2008/0269863 | A1 | 10/2008 | Alexander |

FOREIGN PATENT DOCUMENTS

| | | |
|---|---|---|
| EP | 0760196 | 3/1997 |
| EP | 1273922 | 1/2003 |
| EP | 1 424 095 A1 | 6/2004 |
| EP | 1466576 | 10/2004 |
| JP | 07/255863 | 10/1995 |
| JP | 11/086641 | 3/1999 |
| WO | WO96/28951 | 9/1996 |
| WO | WO97/41923 | 11/1997 |
| WO | WO99/10035 | 3/1999 |
| WO | WO99/19020 | 4/1999 |
| WO | WO99/60370 | 11/1999 |
| WO | WO00/27279 | 5/2000 |
| WO | WO2006/118641 | 11/2000 |
| WO | 0180940 A1 | 11/2001 |
| WO | WO02/83236 | 10/2002 |
| WO | WO03/95022 | 11/2002 |
| WO | WO03/37429 | 5/2003 |
| WO | 03061755 A2 | 7/2003 |
| WO | 03063952 A2 | 8/2003 |
| WO | WO03/63946 | 8/2003 |
| WO | WO03/63948 | 8/2003 |
| WO | WO03/63953 | 8/2003 |
| WO | WO03/63954 | 8/2003 |
| WO | WO03/63955 | 8/2003 |
| WO | WO03/63956 | 8/2003 |
| WO | WO03/63957 | 8/2003 |
| WO | WO03/75797 | 9/2003 |
| WO | WO03/92326 | 11/2003 |
| WO | WO04/52448 | 6/2004 |
| WO | WO04/73040 | 8/2004 |
| WO | WO2005/030322 | 4/2005 |
| WO | 2005102447 A1 | 11/2005 |
| WO | WO2005/102444 | 11/2005 |
| WO | WO2005/102445 | 11/2005 |
| WO | WO2005/102446 | 11/2005 |
| WO | WO06/31317 | 3/2006 |
| WO | WO2006/093685 | 9/2006 |
| WO | WO2006/093686 | 9/2006 |
| WO | WO2006/118640 | 11/2006 |
| WO | WO2008/100839 | 8/2008 |
| WO | WO2008/100840 | 8/2008 |
| WO | WO2008/134196 | 11/2008 |

OTHER PUBLICATIONS

Chung, D.D.L., Comparison of submicron-diameter carbon filaments and conventional carbon fibers as fillers in composite materials, Carbon 39 (2001), pp. 1119-1125, 2001 Elsevier Science Ltd.

Jou, W.S., A Novel Structure of Woven Continuous-Carbon Fiber Composites with High Electromagnetic Shielding, Journal of Electronic Materials, vol. 33, No. 3, Mar. 1, 2004, pp. 162-170(9), Minerals, Metals & Materials Society, http://findarticles.com/p/articles/mi_qa3776/is_200403/ai_n9405582/print.

Chung D, "Carbon Fiber Composites", 1994, chapter 1, p. 8, table 1.2, Elsevier, ISBN: 978-0-7506-9169-7.

International Search Report and Written Opinion, dated Jun. 27, 2008, 12 pages.

Baker et al., "Evaluation of Specific Absorption Rates as a Dosimeter of MRI-Related Implant Heating", Journal of Magnetic Resonance Imaging 20:315-320 (2004).

Baker, K., et al., "Neurostimulation Systems: Assessment of Magnetic Field Interactions Associated with 1.5 and 3-Tesla MR Systems", J. Magn. Reson. Imaging, Jan. 2005, 21(1);72-7.

Finelli, D., et al., "MRI Imaging-Related Heating of Deep Brain Stimulation Electrodes: In Vitro Study", AJNR AM. J. Neuroadiol 23:1, Nov./Dec. 2002.

International Search Report for PCT/US04/031638.
International Search Report for PCT/US04/040082.
International Search Report for PCT/US04/041201.
International Search Report for PCT/US04/042081.
International Search Report for PCT/US05/000322.
International Search Report for PCT/US06/005535.
International Search Report for PCT/US08/053540.
International Search Report for PCT/US08/053541.
International Search Report for PCT/US08/059358.
International Search Report for PCT/US06/005539.
International Search Report for PCT/US06/006754.
International Search Report for PCT/US06/006755.

Kolin, et al., "An Electromagnetic Catheter Flow Meter for Determination of Blood Flow in Major Arteries," Department of Biophysics, Physiology, and Radiology, University of California School of Medicine (Los Angeles) Jan. 19, 1988, Proc. N.A.S. vol. 59, pp. 808-815.

Kolin, et al., "An Electromagnetic Intravascular Blood-Flow Sensor", Department of Biophysics, University of California School of Medicine (Los Angeles), Mar. 20, 1967, Proc. N.A.S., vol. 57, pp. 1331-1337.

Kolin, et al., "Miniaturization of the Electromagnetic Blood Flow Meter and its Use for the Recording of Circulatory Responses of Conscious Animals to Sensory Stimuli", Department of Biophysics, University of California at Los Angeles, Aug. 1959, Proc. N.A.S. vol. 45(8), pp. 1312-1321.

Medtronic Activa Product Family and Procedure Solution Brochure.
Medtronic Neurostimulation Systems Brochure.
Quick et al., "Endourethral MRI", Magnetic Resonance in Medicine, 45:138-146, 2001.

(56) References Cited

OTHER PUBLICATIONS

Rezai, A., et al., "Neurostimulation System Used for Deep Brain Stimulation (DBS): MR Safety Issues and Implications of Failing to Follow Safety Recommendations" Investigative Radiology, May 2004, vol. 39, Issue 5, pp. 300-303.
Rezai, A., et al., "Neurostimulation Systems for Deep Brain Stimulation In Vitro Evaluation of Magnetic Resonance Imaging-Related Healing at 1.5 Tesla", Journal of Magnetic Reson. Imaging 2002; 15:241-50.
U.S. Appl. No. 11/674,992: non-final office action dated Mar. 19, 2009.
U.S. Appl. No. 11/674,992: final office action dated Oct. 29, 2009.
U.S. Appl. No. 10/945,739 non-final office action dated Aug. 23, 2006.
U.S. Appl. No. 10/945,739 response to non-final office action dated Aug. 23, 2006.
U.S. Appl. No. 10/945,739: non-final office action dated Feb. 20, 2007.
U.S. Appl. No. 10/945,739: response to non-final dated Feb. 20, 2007.
U.S. Appl. No. 10/945,739: non-final office action dated Dec. 6, 2007.
U.S. Appl. No. 10/945,739: response to non-final office action dated Dec. 6, 2007.
U.S. Appl. No. 10/945,739: final office action dated May 1, 2008.
U.S. Appl. No. 10/945,739: RCE and response to final office action dated May 1, 2008.
U.S. Appl. No. 10/945,739: corrected amendment dated May 23, 2008.
U.S. Appl. No. 10/945,739: advisory action dated Jul. 28, 2008.
U.S. Appl. No. 10/945,739: non-final office action dated Aug. 19, 2008.
U.S. Appl. No. 10/945,739: response to non-final office action dated Aug. 19, 2008.
U.S. Appl. No. 10/945,739: final office action dated May 22, 2009.
U.S. Appl. No. 10/945,739: RCE and response to final office action dated May 22, 2009.
U.S. Appl. No. 10/945,739: non-final office action dated Sep. 29, 2009.
U.S. Appl. No. 10/945,739: response to non-final office action dated Sep. 28, 2009.
U.S. Appl. No. 10/946,968: non-final office action dated Aug. 29, 2006.
U.S. Appl. No. 10/946,968: response to non-final office action dated Aug. 29, 2006.
U.S. Appl. No. 10/946,968: final rejection dated Apr. 20, 2007.
U.S. Appl. No. 10/981,092: restriction requirement dated Aug. 25, 2006.
U.S. Appl. No. 10/981,092: response to restriction requirement dated Aug. 25, 2006.
U.S. Appl. No. 10/993,195: restriction requirement dated Oct. 27, 2006.
U.S. Appl. No. 10/993,195: response to restriction requirement dated Oct. 27, 2006.
U.S. Appl. No. 10/993,195: non-final office action dated Dec. 6, 2006.
U.S. Appl. No. 10/993,195: response to non-final office action dated Dec. 6, 2006.
U.S. Appl. No. 10/993,195: final office action dated May 8, 2007.
U.S. Appl. No. 10/993,195: response to final office action dated May 8, 2007.
U.S. Appl. No. 10/993,195: non-final office action dated Jul. 26, 2007.
U.S. Appl. No. 10/993,195: response to non-final office action dated Jul. 26, 2007.
U.S. Appl. No. 10/993,195: non-final office action dated May 30, 2008.
U.S. Appl. No. 10/993,195: response to non-final office action dated May 30, 2008.
U.S. Appl. No. 10/993,195: non-final office action dated Feb. 25, 2009.
U.S. Appl. No. 10/993,195: response to non-final office action dated Feb. 25, 2009.
U.S. Appl. No. 10/993,195: final office action dated Oct. 6, 2009.
U.S. Appl. No. 10/993,195: response to final office action dated Oct. 6, 2009.
U.S. Appl. No. 10/993,195: advisory action dated Dec. 18, 2009.
U.S. Appl. No. 10/993,195: pre-appeal brief dated Feb. 5, 2010.
U.S. Appl. No. 10/993,195: panel decision dated Mar. 10, 2010.
U.S. Appl. No. 11/009,862: restriction requirement dated Aug. 8, 2007.
U.S. Appl. No. 11/009,862: response to restriction requirement dated Aug. 8, 2007.
U.S. Appl. No. 11/009,862: non-final office action dated Oct. 2, 2007.
U.S. Appl. No. 11/009,862: response to non final office action dated Oct. 2, 2007.
U.S. Appl. No. 11/009,862: final office action dated May 22, 2008.
U.S. Appl. No. 11/009,862: RCE and response to final office action dated May 22, 2008.
U.S. Appl. No. 11/009,862: non-final office action dated Oct. 27, 2008.
U.S. Appl. No. 11/009,862: response to non-final office action dated Oct. 27, 2008.
U.S. Appl. No. 11/009,862: final office action dated Apr. 9, 2009.
U.S. Appl. No. 11/009,862: RCE and response to final office action dated Apr. 9, 2009.
U.S. Appl. No. 11/009,862: non-final office action dated Aug. 3, 2009.
U.S. Appl. No. 11/009,862: response to non-final office action dated Aug. 3, 2009.
U.S. Appl. No. 11/009,862: final office action dated Feb. 25, 2010.
U.S. Appl. No. 11/009,862: RCE and response to final office action dated Feb. 25, 2010.
U.S. Appl. No. 11/067,024: requirement restriction dated, Mar. 6, 2008.
U.S. Appl. No. 11/067,024: response to restriction requirement dated, Mar. 6, 2008.
U.S. Appl. No. 11/067,024: non-final office action dated, Apr. 7, 2008.
U.S. Appl. No. 11/067,024: response to non-final office action dated Apr. 7, 2008.
U.S. Appl. No. 11/067,024: final office action dated Mar. 18, 2009.
U.S. Appl. No. 11/067,024: RCE and response to final office action dated Mar. 18, 2009.
U.S. Appl. No. 11/067,024: non-final office action dated Jul. 6, 2009.
U.S. Appl. No. 11/067,024: response to non final office action dated Jul. 6, 2009.
U.S. Appl. No. 11/071,136: non-final office action dated Feb. 23, 2007.
U.S. Appl. No. 11/071,136: response to non-final office action dated Feb. 23, 2007.
U.S. Appl. No. 11/071,136: final office action dated Aug. 1, 2007.
U.S. Appl. No. 11/071,136: response to final office action dated Aug. 1, 2007.
U.S. Appl. No. 11/071,136: non-final office action dated Oct. 19, 2007.
U.S. Appl. No. 11/071,136: response to non-final office action dated, Oct. 19, 2007.
U.S. Appl. No. 11/071,136: final office action dated May 14, 2008.
U.S. Appl. No. 11/071,136: RCE and response to final office action dated May 14, 2008.
U.S. Appl. No. 11/071,136: restriction requirement dated Oct. 31, 2008.
U.S. Appl. No. 11/071,136: response to restriction requirement dated Oct. 31, 2008.
U.S. Appl. No. 11/071,136: non-final office action dated Feb. 13, 2009.
U.S. Appl. No. 11/071,136: response to non-final office action dated Feb. 13, 2009.
U.S. Appl. No. 11/071,136: final office action dated Feb. 19, 2010.

(56) References Cited

OTHER PUBLICATIONS

U.S. Appl. No. 11/071,136: RCE and response to final office action dated Feb. 19, 2010.
U.S. Appl. No. 11/117,882: non-final office action dated Feb. 20, 2008.
U.S. Appl. No. 11/117,882: response to non-final office action dated Feb. 20, 2008.
U.S. Appl. No. 11/117,882: final office action dated Aug. 26, 2008.
U.S. Appl. No. 11/117,882: RCE and response to final office action dated Aug. 26, 2008.
U.S. Appl. No. 11/117,882: non-final office action dated Mar. 23, 2009.
U.S. Appl. No. 11/117,882: response to non final office action dated Mar. 23, 2009.
U.S. Appl. No. 11/117,882: final office action dated Oct. 21, 2009.
U.S. Appl. No. 11/117,882: RCE and response to final office action dated Oct. 21, 2009.
U.S. Appl. No. 11/117,882: non-final office action dated Mar. 1, 2010.
U.S. Appl. No. 11/117,882: response to non-final office action dated Mar. 1, 2010.
U.S. Appl. No. 11/117,894: non-final office action dated Dec. 11, 2007.
U.S. Appl. No. 11/117,894: response to non-final office action dated Dec. 11, 2007.
U.S. Appl. No. 11/117,894: final office action dated May 2, 2008.
U.S. Appl. No. 11/117,894: RCE and response to final office action dated May 2, 2008.
U.S. Appl. No. 11/117,894: non-final office action dated Dec. 2, 2008.
U.S. Appl. No. 11/117,894: response to non-final office action dated Dec. 2, 2008.
U.S. Appl. No. 11/117,894: final office action dated May 28, 2009.
U.S. Appl. No. 11/117,894: RCE and response to final office action dated May 28, 2009.
U.S. Appl. No. 11/117,894: restriction requirement dated Nov. 24, 2009.
U.S. Appl. No. 11/117,894: response to restriction requirement dated Nov. 24, 2009.
U.S. Appl. No. 11/117,894: non-final office action dated Mar. 31, 2010.
U.S. Appl. No. 11/117,894: response to non-final office action dated Mar. 31, 2010.
U.S. Appl. No. 11/346,486: restriction requirement dated Aug. 6, 2008.
U.S. Appl. No. 11/346,486: response to restriction requirement dated Aug. 6, 2008.
U.S. Appl. No. 11/346,486: non-final office action dated Sep. 26, 2008.
U.S. Appl. No. 11/346,486: response to non-final office action dated Sep. 26, 2008.
U.S. Appl. No. 11/346,486: non-final office action dated Apr. 2, 2009.
U.S. Appl. No. 11/346,486: response to non-final office acdon dated Apr. 2, 2009.
U.S. Appl. No. 11/346,486: final office action dated Jan. 12, 2010.
U.S. Appl. No. 11/346,486: RCE and response to final office action dated Jan. 12, 2010.
U.S. Appl. No. 11/674,992: response to non final office action dated Mar. 19, 2009.
U.S. Appl. No. 11/674,992: RCE and response to final office action dated Oct. 29, 2009.
U.S. Appl. No. 11/739,787: non-final office action dated Jun. 12, 2009.
U.S. Appl. No. 11/739,787: response to non-final office action dated Jun. 12, 2009.
U.S. Appl. No. 11/739,787: non-final office action dated Jan. 11, 2010.
U.S. Appl. No. 11/739,787: response to non-final office action dated Jan. 11, 2010.
U.S. Appl. No. 11/739,787: final office action dated May 13, 2010.
U.S. Appl. No. 11/739,787: response to final office action dated May 13, 2010.
PCT/US04/42081: search report and written opinion dated Mar. 14, 2005.
PCT/US04/42081: response to written opinion dated Mar. 14, 2005.
PCT/US04/42081: second written or dated Mar. 10, 2006.
PCT/US04/42081: response to second written opinion dated Mar. 10, 2006.
PCT/US04/42081: IPRP.
PCT/US06/05539: search report and written opinion dated Feb. 15, 2006.
PCT/US06/05539: response to written opinion dated Feb. 15, 2006.
PCT/US06/05539: IPRP dated Jun. 28, 2007.
PCT/US06/06754: search report and written opinion dated Jul. 24, 2006.
PCT/US06/06754: response to written opinion dated Jul. 24, 2006.
PCT/US06/06754: IPRP dated Jun. 2, 2007.
PCT/US06/06755: search report and written opinion dated Jul. 24, 2006.
PCT/US06/06755: response to written opinion dated Jul. 24, 2006.
PCT/US06/06755: IPRP dated Aug. 21, 2007.
PCT/US08/53540: search report and written opinion dated Jul. 17, 2008.
PCT/US08/53540: IPRP dated Aug. 27, 2009.
PCT/US08/53541: search report and written opinion dated Jun. 27, 2008.
PCT/US08/59358: search report and written opinion dated Jul. 14, 2008.
PCT/US04/31638: search report and written opinion dated Jan. 17, 2005.
PCT/US04/31638: IPRP dated Apr. 6, 2006.
PCT/US04/40082: search report and written opinion dated Mar. 15, 2005.
PCT/US04/40082: response to written opinion dated Mar. 15, 2005.
PCT/US04/40082: IPRP dated Mar. 5, 2006.
PCT/US04/041201: search report and written opinion dated Mar. 16, 2005.
PCT/US05/00322: search report and written opinion dated Mar. 30, 2005.
PCT/US05/00322: response to written opinion dated Mar. 30, 2005.
PCT/US05/00322: second written opinion dated Apr. 18, 2006.
PCT/US05/00322: response to second written opinion dated Apr. 18, 2006.
PCT/US05/00322: IPRP dated Jul. 5, 2006.
PCT/US06/05535: search report and written opinion dated May 31, 2006.
PCT/US06/05535: IPRP dated Sep. 7, 2007.

* cited by examiner

CONTINUOUS CONDUCTIVE MATERIALS FOR ELECTROMAGNETIC SHIELDING

FIELD

The present invention relates generally to medical devices, and, more particularly, to reducing the effects of electromagnetic radiation on such medical devices.

BACKGROUND

Since their earliest inception, implantable medical devices (IMDs) have continually been advanced in significant ways. Today, IMDs include therapeutic and diagnostic devices, such as pacemakers, cardioverter/defibrillators, hemodynamic monitors, neurostimulators, and drug administering devices, as well as other devices for alleviating the adverse effects of various health ailments.

As is known, modern electrical therapeutic and diagnostic devices for the heart and other areas of the body generally include an electrical connection between the device and the body. This connection is usually provided by at least one medical electrical lead. For example, a neurostimulator delivers mild electrical impulses to neural tissue using one or more electrical leads. In turn, such neurostimulation often results in effective pain relief and a reduction in the use of pain medications and/or repeat surgeries. Each electrical lead used with such devices typically takes the form of a long, generally straight, flexible, insulated conductor. At its proximal end, the lead is typically connected to a connector of the device, which also may be implanted within the patient's body. Generally, one or more electrodes are located at or near the distal end of the lead and are attached to, or otherwise come in contact with, the body. Such devices may be controlled by a physician or a patient through the use of an external programmer.

It is well known that, if not shielded sufficiently, the implanted leads of medical devices can be adversely affected when a patient is exposed to alternating electromagnetic fields. Alternating electromagnetic fields can generally stem from any of a number of radio-frequency radiation sources, e.g., magnetic resonance imaging (MRI) systems as described below. As such, if an implanted medical lead is not sufficiently shielded, electromagnetic fields can induce an electric current within a conductor of the lead. In turn, such an implanted electrical lead would act as an antenna, resulting in an electrical current that flows from the electrode of the lead and through body tissue. Because the tissue area associated with electrode contact may be very small, the current densities may be high, which can result in tissue heating that may cause damage.

There can be other limitations associated with exposing implanted leads of medical devices to electromagnetic fields and/or radio-frequency energy if the leads are not sufficiently shielded therefrom. As is known, a sudden burst of radio-frequency energy can cause an electric pulse within the lead. The medical device, as should be appreciated, can sense the imposed voltage on the lead, and in turn, may cause the device to respond inappropriately, resulting in the wrong therapy being administered to the patient at that time or in the future. For example, with respect to cardiac IMDs, inappropriate therapy modification may be one response of the IMD, which can involve changing the rate or thresholds associated with pacing pulses.

As is known, magnetic resonance imaging (MRI) is an anatomical imaging tool which utilizes non-ionizing radiation (i.e., no x-rays or gamma rays) and provides a non-invasive method for the examination of internal structure and function. For example, MRI permits the study of the overall function of the heart in three dimensions significantly better than any other imaging method. Furthermore, MRI scanning is widely used in the diagnosis of diseases and injuries to the head. Magnetic resonance spectroscopic imaging (MRSI) systems are also known and are herein intended to be included within the terminology "MRI" systems or scanners. These MRI systems can be used to give valuable diagnostic information, but also subject the patient to significant alternating electromagnetic fields and/or radio-frequency energy, which may result in one or more of the undesirable effects described above with respect to IMDs or medical devices using implanted leads.

A variety of different coverings have been used for implantable leads of medical devices to overcome the above limitations. Some coverings have involved metal or metal alloy wires being braided around the lead, thereby forming a shield having a large conductive surface area. Such metal wires are selected primarily for their high conductive properties. While the wire lead coverings have been used to reduce the effects of electromagnetic radiation, the lead coverings have been found to present certain limitations, e.g., with respect to minimum sizes that can achieved, high production costs, etc. What is needed is apparatus used to reduce the potential adverse effects to medical devices, and in particular, to implantable electrical leads of the devices, when subjected to electromagnetic radiation, while further overcoming one or more of the limitations facing the wire shield coverings marketed to date.

BRIEF SUMMARY OF THE INVENTION

Embodiments of the invention relate to medical electrical leads having a conductor assembly covered by an insulating layer, and a shield covering positioned adjacent or proximate to at least a portion of the insulating layer in order to shield the conductor assembly from one or more electromagnetic fields. The shield covering is formed of a material that is electrically conductive, where the material is in a wrapped or woven form. The material is selected so as to have an effective combination of small size and high conductive surface area, e.g., as opposed to metal wire or coatings thinner than metal wire. As such, the shield covering exhibits sufficient conductivity in the presence of one or more high frequency electromagnetic fields so that interference to the operation of the conductor assembly is minimized. The material can have a coating formed of one or more metals. The material can include carbon. In turn, the carbon can be formed of one or more of carbon fiber, carbon nanofiber, and single or multi-walled carbon nanotube.

DETAILED DESCRIPTION OF THE PREFERRED EMBODIMENTS

Figure 1:
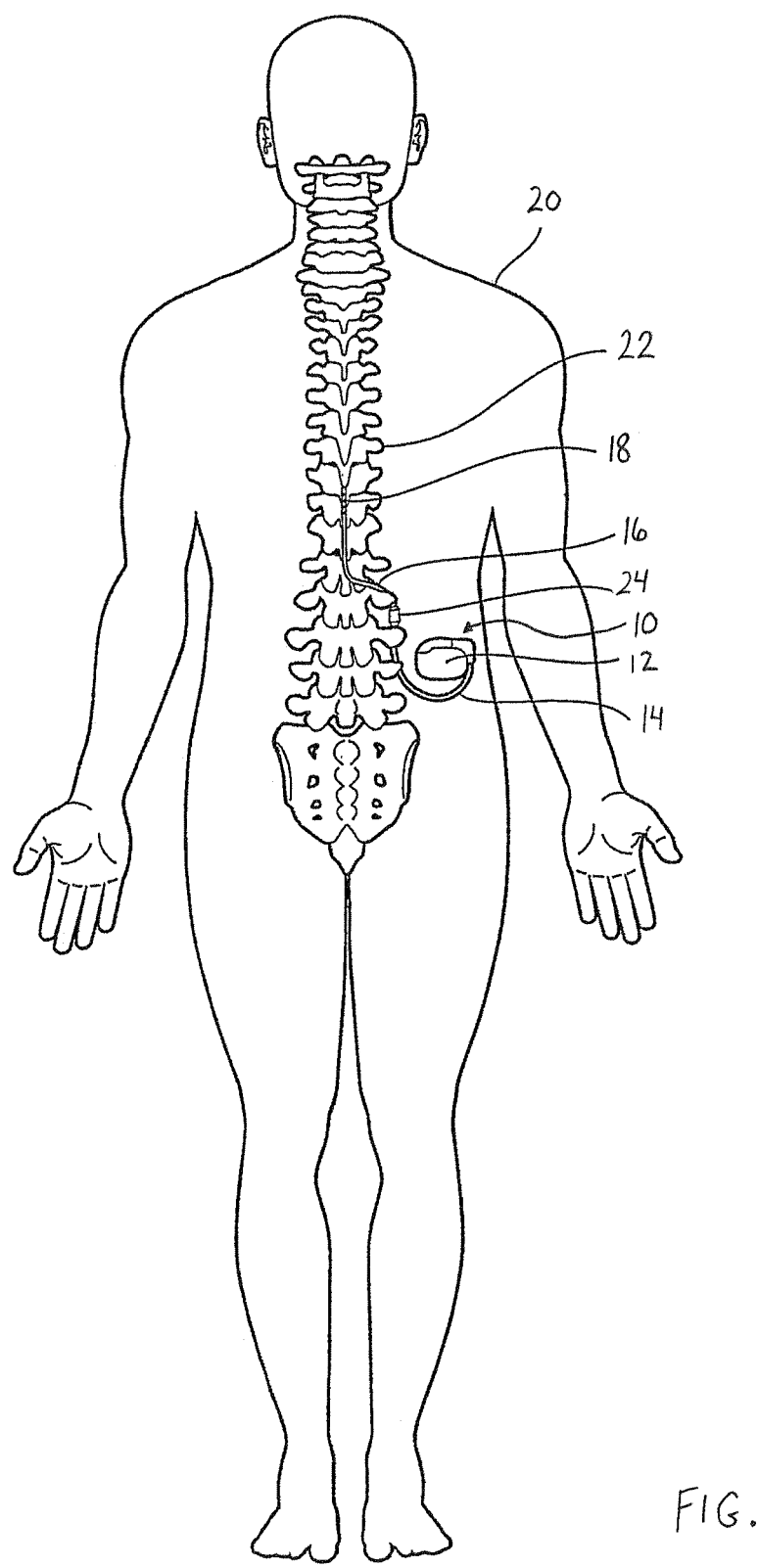
FIG. 1 is a perspective view of an exemplary IMD as provided in a patient in accordance with certain embodiments of the invention.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

Embodiments of the invention relate to medical devices, and specifically relate to shield coverings for leads extending between the devices and the patient. Embodiments described and illustrated herein pertain to implantable medical devices (IMDs); however, the invention can extend to any lead-bearing medical device, whether implantable or not. Furthermore, while the embodiments provided herein relate to certain IMDs, it should be appreciated that such embodiments are exemplary in nature. As such, the invention is not limited to any particular IMD, but instead is applicable to any IMD, including therapeutic and diagnostic devices, such as pacemakers, cardioverter/defibrillators, hemodynamic monitors, neurostimulators, and drug administering devices, as well as other devices for alleviating the adverse effects of various health ailments.

FIG. 1 illustrates an exemplary IMD in accordance with certain embodiments of the invention. The IMD 10 shown is a typical spinal cord stimulation (SCS) system and includes a pulse generator such as a SCS neurostimulator 12, a lead extension 14 having a proximal end coupled to the neurostimulator 12, and a lead 16 having a proximal end coupled to a distal end of the extension 14 and having a distal end coupled to one or more electrodes 18. The neurostimulator 12 is typically placed in the abdomen of a patient 20, and the lead 18 is placed somewhere along the patient's spinal cord 22. While only shown with a single lead 18, it is to be appreciated that the IMD 10, in certain embodiments, can have a plurality of leads. Such a system may also include a physician programmer and a patient programmer (not shown).

The neurostimulator 12 may be considered to be an implantable pulse generator and capable of generating multiple pulses occurring either simultaneously or one pulse shifting in time with respect to the other, and having independently varying amplitudes and pulse widths. The neurostimulator 12 contains a power source and electronics for sending precise, electrical pulses to the spinal cord 22 to provide the desired treatment therapy. While the neurostimulator 12 typically provides electrical stimulation by way of pulses, other forms of stimulation may be used such as continuous electrical stimulation.

The lead 16 includes one or more insulated electrical conductors each coupled at their proximal end to a connector 24 and to the electrodes 18 (or contacts) at its distal end. As is known, some leads are designed to be inserted into a patient percutaneously and some are designed to be surgically implanted. In certain embodiments, the lead 16 may contain a paddle at its distant end for housing the electrodes 18. In alternate embodiments, the electrodes 20 may comprise one or more ring contacts at the distal end of the lead 16.

While the lead 16 is shown as being implanted in position to stimulate a specific site in the spinal cord 22, it could also be positioned along the peripheral nerve or adjacent neural tissue ganglia or may be positioned to stimulate muscle tissue. Furthermore, electrodes 18 (or contacts) may be epidural, intrathecal or placed into spinal cord 22 itself. Effective spinal cord stimulation may be achieved by any of these lead placements. While the lead connector at proximal end of the lead 16 may be coupled directly to the neurostimulator 12, the lead connector is typically coupled to the lead extension 14 as is shown in FIG. 1.

Figure 2:
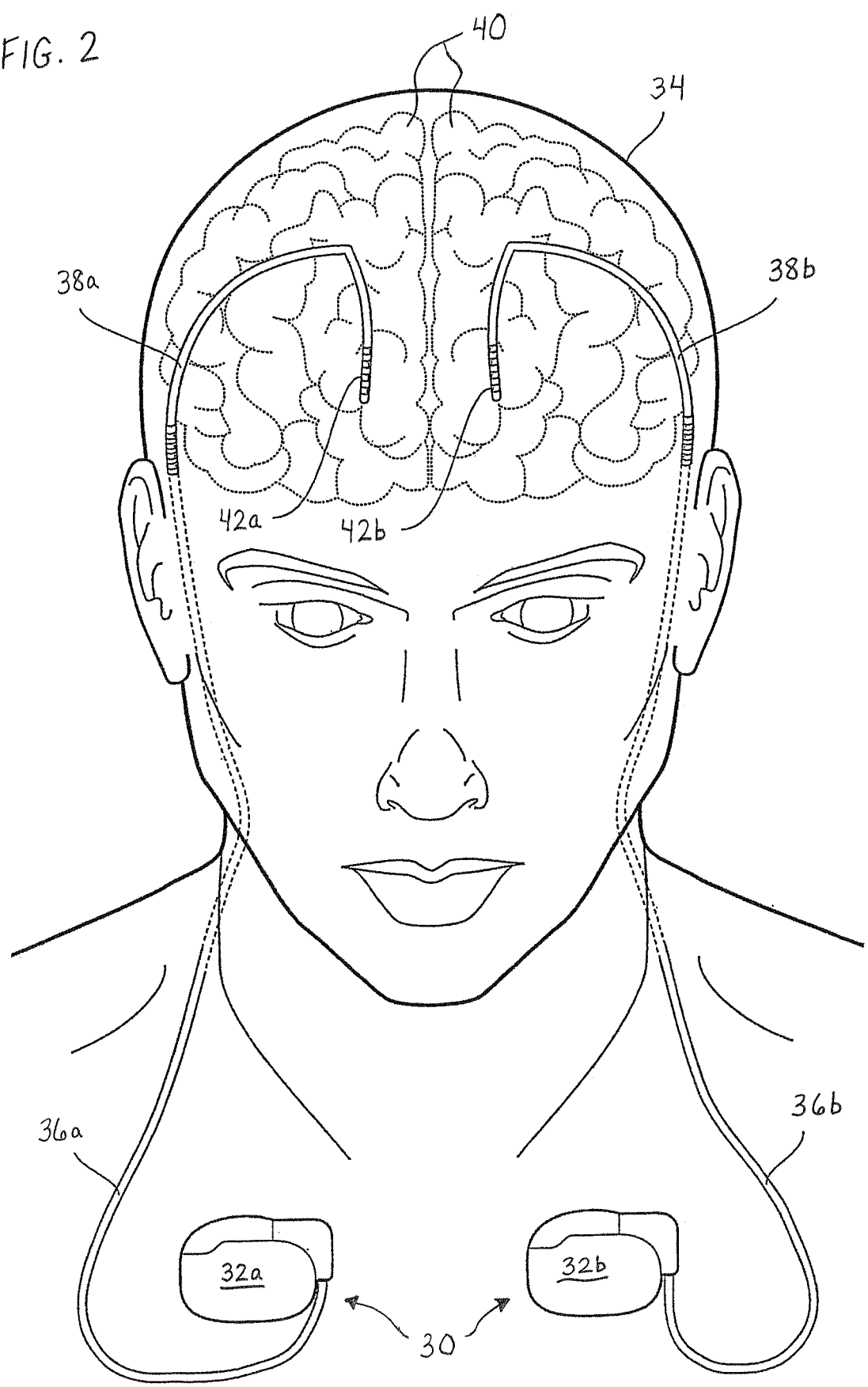
FIG. 2 is a perspective view of another exemplary IMD as provided in a patient in accordance with certain embodiments of the invention.

FIG. 2 illustrates another exemplary IMD in accordance with certain embodiments of the invention. The IMD 30 shown is a typical deep brain stimulation (DBS) system spinal cord stimulation (SCS) system and includes substantially the same components as does an SCS; that is, at least one neurostimulator, at least one extension, and at least one stimulation lead containing one or more electrodes. As can be seen, each neurostimulator 32a and 32b is implanted in the pectoral region of patient 34. Corresponding extensions 36a and 36b are deployed up through the patient's neck, and corresponding leads 38a and 38b are implanted in the patient's brain 40 as is shown at 42a and 42b. As can be seen, each of the leads 38 is connected to its respective extension 36 just above the ear on both sides of the patient 34.

Figure 3:
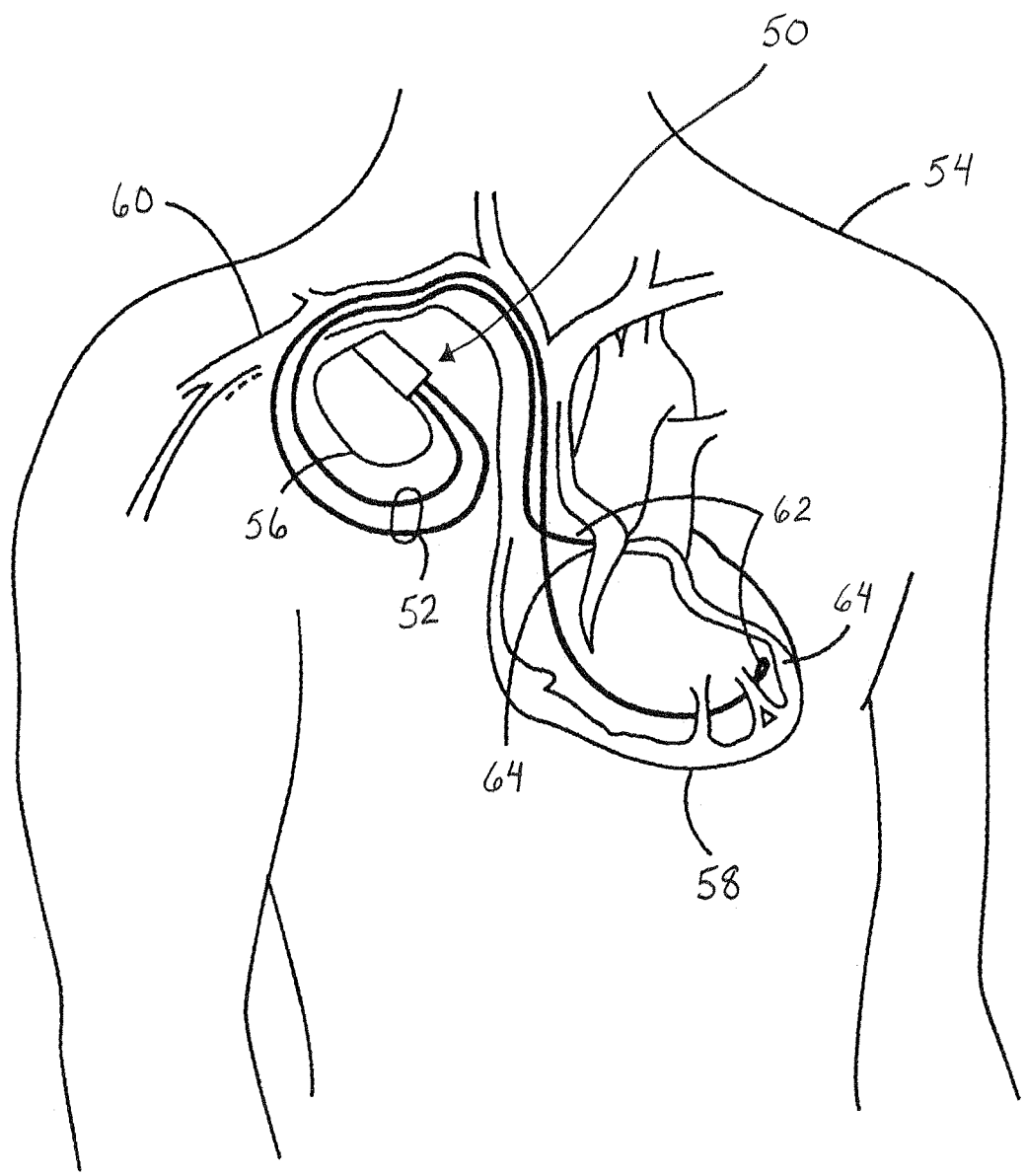
FIG. 3 is a perspective view of a further exemplary IMD as provided in a patient in accordance with certain embodiments of the invention.

FIG. 3 illustrates a further exemplary IMD in accordance with certain embodiments of the invention. The IMD 50 is a cardiac medical device, exemplarily shown as a pacemaker, and includes one or more leads 52 implanted in a patient 54. The leads 52 extend from the pacemaker can 56 and lead into the patient's heart 58 via a vein 60. Located generally near distal ends 62 of the leads 52 are one or more exposed conductive electrodes 64 that are attached to the heart tissue for sensing cardiac activity, delivering electrical pacing stimuli, and/or providing a cardioversion/defibrillation shock to the heart 58. The contact area between the electrodes 64 and the tissue of the heart 58 may be very small as compared, for example, to the contact area between the IMD 50 and the patient's body.

Implantable leads of IMDs similar to those described above in FIGS. 1-3, as well as implantable leads of other medical devices, have been equipped to reduce the effect from electromagnetic fields and/or radio-frequency energy, e.g., which can stem from MRI systems. As described above, one method of reducing this effect is through the use of conductive metal and metal alloy wires having high electrical conductivity properties. For example, wire, composed of metals such as Pt, Pd, Ti, Ag, Au, MP35N and their alloys, can be braided around the electrical leads, thereby providing a protective shield for the leads. Such metal wire would be advantageous due to its good conductivity properties and high surface area for such conductivity.

Other methods of reducing interference from electromagnetic fields and/or radio-frequency energy from IMD leads have involved the use of coatings, formed of metal or otherwise. In such methods, a thin conductive shield coating can be attached in sheet form, or alternatively, to be sputtered, on a lead. In such cases, the thin conductive coating can be provided at a much reduced thickness than metal wire (e.g., generally 2 µm or less). In turn, the shield coatings are found to not significantly restrict the flexibility or increase the diameter of the lead. In addition, the thinness of the sputtered metal provides less resistance for the coating to one or more surrounding electromagnetic energy fields. Unfortunately, all of the above described methods have drawbacks.

As is known, when a static electrical field is applied to a conductor, the mobile charges therein, e.g., the electrons, are found to move and create a direct current (DC), which is uniformly distributed on the entire cross section of the conductor, resulting in a uniform current density. However, when an electromagnetic field is imposed on such a conductor, the mobile charges therein are found to oscillate back and forth with the same frequency as the impinging fields. The movement of these charges constitutes an alternating current (AC). Due to the attenuation of the electromagnetic waves in the conductor, the conductor's current density is greatest at the conductor's surface and declines exponentially as a function of depth. The decline in current density versus depth is known as the skin effect and the skin depth is a measure of the distance over which the current falls from its value at the conductor's surface.

With respect to metal wire lead coverings, the metal wire is generally limited with respect to the minimum diameter that it can be produced at (e.g., generally around 20 µm). Accordingly, metal wire provides an inefficient electromagnetic shield at high frequencies due to skin effect, as described herein. In addition, metal wire generally has a high manufacturing cost relative to other conductive materials and is prone to fretting fatigue. In cases where thin conductive coatings are used (e.g., attached to the lead in sheet form or via sputtering), the coatings, because they are thin, are limited as to how much electromagnetic radiation they can attenuate. In addition, the thin coatings have far less surface area than what can be achieved when using metal wire, thereby limiting the coating's overall conductivity. As such, a more effective lead covering alternative would be useful. In particular, the lead covering alternative would have an effective combination of both size and surface area to provide a protective lead covering for enhancing its shielding effect with respect to radiation from one or more electromagnetic fields.

One effective alternative to such metal wire or thin coatings is provided herein as a non-metallic conductive material formed to extend continuously over the IMD lead. In certain embodiments, the non-metallic conductive material can be carbon, e.g., synthesized carbon or graphite; however, the invention should not be limited to such. Instead, any other non-metallic conductive material demonstrating similar advantageous properties, as described herein with respect to carbon, may be alternatively used. In certain embodiments, the carbon can formed as continuous carbon fiber. As should be appreciated, continuous carbon fiber is generally not formed of a single conductive member (like the metal wire described above), but instead a plurality of conductive members or strands, which are bundled together. For example, carbon fiber, having strands with diameter ranging in size from about 5 µm to about 12 µm, are commercially available and practical to produce. In certain embodiments, the non-metallic conductive material has an outer diameter that is preferably no greater than about 20 µm (generally representing minimum diameter of metal wire), and more preferably, no greater than about 12 µm.

As should be appreciated, when continuous carbon fiber is wrapped or woven around a lead and used as a shield covering for electromagnetic radiation, it provides greater thickness for attenuation and higher surface area for conductivity than the thin conductive coatings described above. In addition, because it is wrapped or woven around the lead, the continuous carbon fiber generally provides the lead greater flexibility than what it would have if covered with a thin coating of conductive material.

In comparison to metal wire, continuous carbon fiber is relatively inexpensive to produce. Additionally, the yield strength and fatigue life for the carbon fiber is found to be relatively high. In turn, such fiber has a low coefficient of friction which would cause less potential of fretting fatigue as compared to metal wires. Additionally, while the outer diameter of the continuous carbon fiber may approach or even exceed the minimum diameter of commercially available metal wire, each individual strand of carbon fiber functions as a separate shielding conductor. As such, based on their smaller diameter, the carbon fiber strands are found to be significantly less susceptible to the skin effect at high frequencies than metal wire, as described below.

Figure 4:
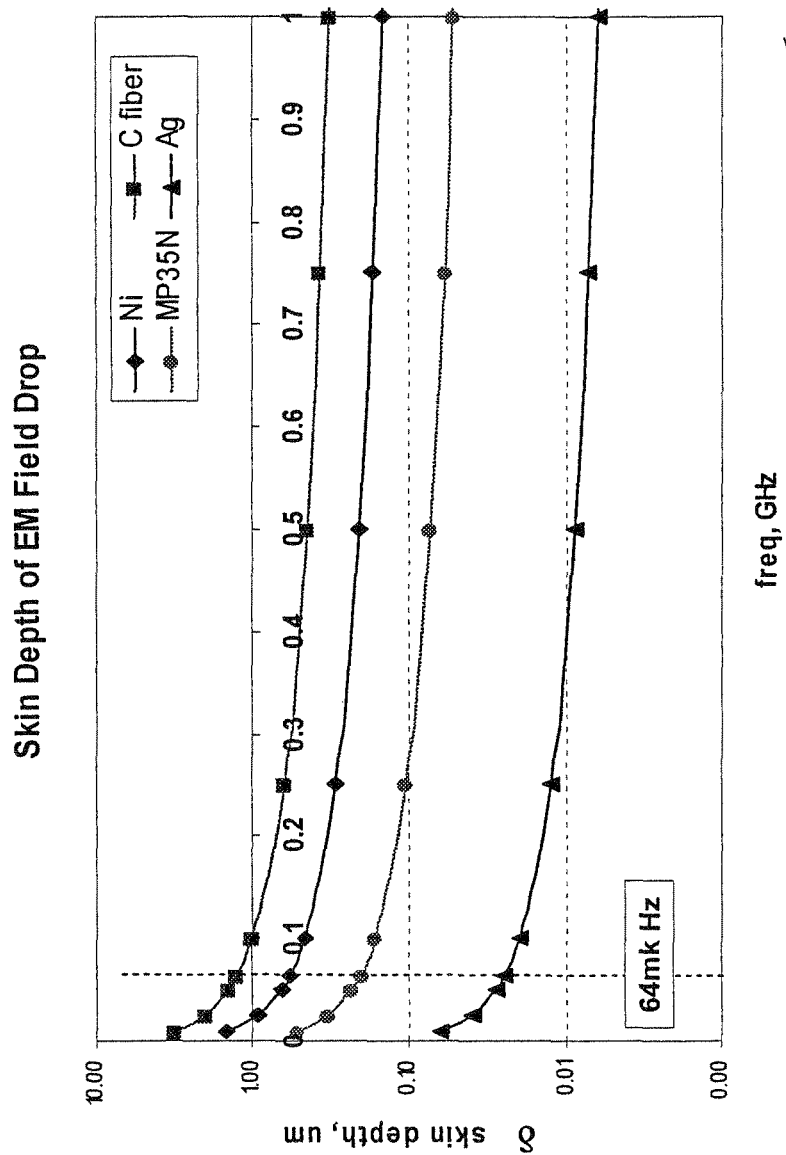
FIG. 4 is a plot generally showing skin depth for carbon and metals at high frequencies of electromagnetic fields.

FIG. 4 is a plot illustrating skin effect for carbon and a number of metals, illustrating the relationship described above. Specifically, the plot shows skin depth (in µm) for carbon and a number of metals at high frequencies (in GHz) of electromagnetic fields. As illustrated, skin depth for the materials generally decreases as frequency increases (with respect to electromagnetic fields surrounding the materials). Thus, while metals are generally known to exhibit high conductivity, the cross-sectional area of these metals which is actually usable for such purposes is limited due to the skin effect.

As shown, carbon is also limited due to the skin effect, but to a lesser extent than the metals. However, as described above, a carbon fiber strand can be made having a smaller diameter than metal wire. As a result, a larger portion of the cross-sectional area of a carbon fiber strand can generally be used for conductive purposes in comparison to such metal wire. Therefore, a continuous carbon fiber can be found to be more efficient than continuous metal wire, particularly when used as a shield in the presence of high frequency electromagnetic fields. For example, as demonstrated in FIG. 4, skin depth of conductive metals is typically less than 1 µm when the frequency of surrounding electromagnetic fields is about 64 MHz or higher. As such, continuous metal wire, even when its diameter is minimized (e.g., possibly to about 20 µm), is not a very effective shield because much of its cross-sectional area would carry very little current. Conversely, carbon fiber strands can have an outer diameter ranging from about 5 µm to about 12 µm. As such, each strand of the carbon fiber would have a higher percentage of cross section capable of conducting in comparison to metal wire. In turn, each strand would be more efficient than metal wire in its use as a lead shield covering.

As described above, continuous carbon fiber would be preferable to thin coatings because the fiber, when wrapped or woven across the lead, provides greater thickness for attenuation and higher surface area for conductivity. As further described above, continuous carbon fiber would be preferable to continuous metal wire because a higher percentage of the cross-sectional area of the carbon fiber strands can be used for conductivity purposes, particularly in the presence of high frequency electromagnetic fields. Though, even with the above-described greater thickness, higher surface area, and increased efficiency, the carbon is generally less conductive than metal, whether provided as a coating or in wire form. However, as described above, because the carbon fiber is formed of a plurality of strands, the strands function collectively in providing the carbon fiber's conductivity. In turn, the increased efficiency of the carbon strands (as described above with respect to skin depth) in combination with the plurality of strands used in the carbon fiber enables carbon fiber to exhibit good conductivity across the lead.

In certain embodiments, to further enhance the conductivity of the continuous carbon fiber, the carbon fiber can be provided with a metal coating. The metal coating, in certain embodiments, can be provided on the carbon fiber prior to the fiber being wrapped or woven around the electrical lead. In combination, the carbon fiber and metal coating can be used to enhance the shielding effectiveness of the lead covering. The metal coating provides enhanced conductivity for the lead covering, while the carbon fiber provides greater thickness and greater surface area to enhance the attenuation of electromagnetic radiation by the lead covering. Such metal coating, in certain embodiments, can be provided so as to be no greater than about 1 µm. Metalization of carbon fiber, as well as carbon nanofiber and carbon nanotube, can be achieved via physical vapor deposition, chemical vapor deposition, auto-catalytic electroless deposition, or other metallization techniques known to the art. The metal coating can include but is not limited to Ag, Au, Cu, Co, Ni, Pt, Sn, Ta, Ti, Zn, alloys thereof, as well as any combination thereof.

Accordingly, carbon fiber can be used to provide a more effective shield as a lead covering in the presence of electromagnetic fields as opposed to metal wire or thin coatings. In particular, the carbon fiber provides a more efficient material than metal wire, while also providing greater thickness for attenuation and higher surface area for conductivity than thin lead coatings. Further, in certain embodiments, when the carbon fiber is provided with a metal coating, the ensuing lead covering further provides enhanced conductivity. In summary, the carbon fiber can be found to exhibit conductivity in the presence of electromagnetic fields (in particular, high frequency electromagnetic fields) so that interference to the operation of the electrical lead is minimized, as described herein.

Figure 5A:
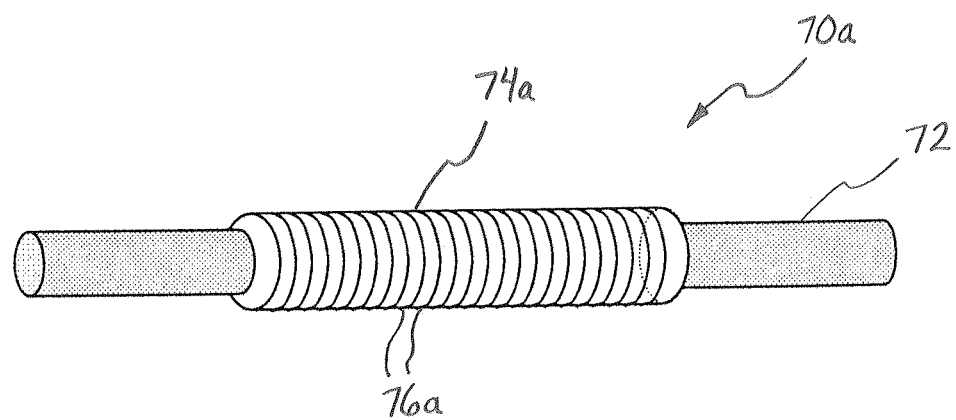
FIG. 5A is a perspective view of a partial implantable lead/extension having a shield covering in accordance with certain embodiments of the invention.
Figure 5B:
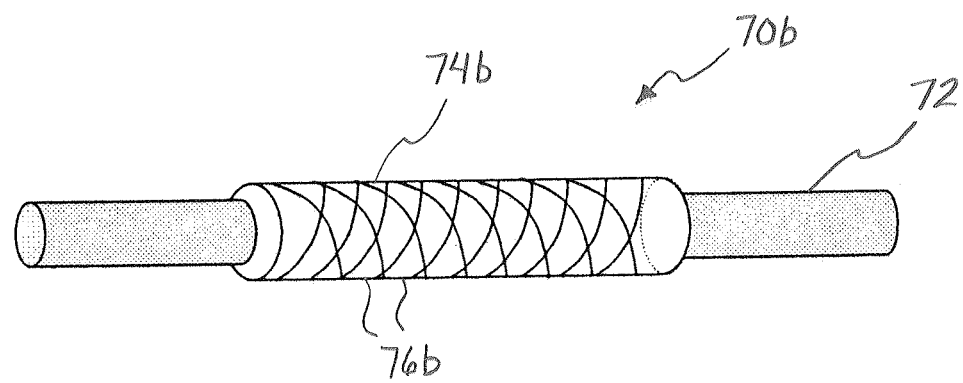
FIG. 5B is a perspective view of a partial implantable lead/extension having a further shield covering in accordance with certain embodiments of the invention.

FIGS. 5A and 5B each illustrate a perspective view of a partial implantable lead/extension having a shield covering in accordance with certain embodiments of the invention. As respectively shown in FIGS. 5A and 5B, the leads/extensions 70a and 70b include conductor assemblies, each having one of more conductors (not shown) covered by an insulating layer 72. As should be appreciated, the one or more conductors can be formed of any suitable metal having conductive properties, such as Cu, Al, Ag, alloys thereof, mixtures thereof, and the like. Further, as should be appreciated, each of the one or more conductors can be configured into one of a wide variety of shapes, e.g., generally straight, helically wound, etc. The insulating layer 72 is generally formed of silicone, a biocompatible polymer such as polyurethane, or any suitable biocompatible, non-conducting material known in the art.

As shown, the leads/extensions 70a and 70b each have a shield covering 74a and 74b, respectively, which function to shield electromagnetic radiation from the lead conductors. In certain embodiments, the shield coverings 74a and 74b are provided as one or more conducting or semiconducting layers. The coverings 74a and 74b are not in direct electrical contact with the conductors of the conductor assemblies of the leads/extensions 70a and 70b, respectively. The coverings 74a and 74b can be in contact with the housing of the medical device (e.g., IMD) from which they stem, where the device can act as an additional surface for dissipation of energy received by the coverings 74a and 74b from electromagnetic waves.

As described above, in certain embodiments, the shield coverings 74a and 74b are formed of a non-metallic conductive material. In certain embodiments, the material is carbon, and formed of carbon fiber. Alternatively or in combination with carbon fiber, the shield coverings 74a and 74b, in certain embodiments, can be composed of one or more of carbon nanofiber and carbon nanotube having one or more of single or multiple walls. Accordingly, in certain embodiments, the shield coverings 74a and 74b are provided having one or more carbon fibers, one or more carbon nanofibers, one or more carbon nanotubes, or any combination thereof. As should be appreciated, carbon fiber, carbon nanofiber, and carbon nanotube (as opposed to metal wire and thin coatings) each have both small diameters for enhanced efficiency (e.g., carbon nanofiber and carbon nanotube generally found to have outer diameters less than about 1 µm) and high surface areas for enhanced conductivity. However, in certain embodiments, carbon fiber may be preferred to carbon nanofiber and carbon nanotube because it is generally found to be less expensive to fabricate and generally easier to control. As should be appreciated, there are many grades of such carbon fibers commercially available. As one skilled in the art would appreciate, the grade of carbon fiber selected is primarily based on the carbon fiber having, or being able to be produced to have, a small diameter (as described above), yet also exhibiting low electrical resistivity and high strength properties.

FIG. 5A illustrates the covering 74a being provided in a wrapped or coiled form on the lead/extension 70a. As such, the covering 74a is provided with a plurality of turns 76a adjacent or proximate to the insulation layer 72, with each of the turns 76a having substantially the same outer diameter. In certain embodiments, as shown, the covering 74a has no overlapping turns 76a. As further shown, in certain embodiments, the covering 74a is generally wound so as have contacting consecutive turns 76a. Alternately, FIG. 5B illustrates the covering 74b being provided in a woven or braided form on the lead/extension 70b. As such, the covering 74b is provided with a plurality of overlapping turns 76b. In certain embodiments, each of the turns 76b has substantially the same outer diameter.

It should be appreciated that the leads/extensions 70a and 70b can be either leads, extensions for leads, or both. For example, with respect to the IMD 10 of FIG. 1, the leads 16, the lead extensions 14, or both, can be equipped with the coverings 74a or 74b. The same holds true for the leads 38a, 38b and extensions 36a, 36b with respect to the IMD 30 of FIG. 2.

Figure 6:
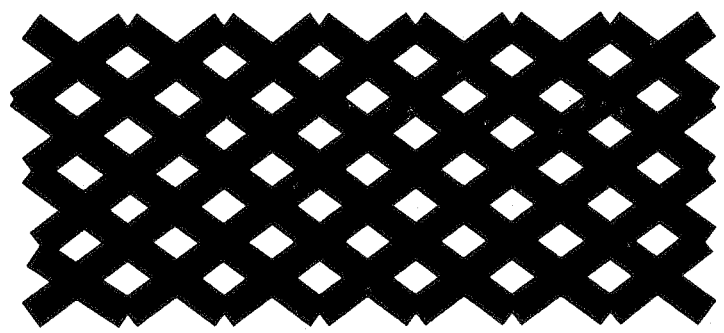
FIG. 6 is an enlarged elevation view of braided metal wire as typically used for covering leads.

By way of comparison, FIG. 6 shows an enlarged top view of braided wire as typically used for covering leads. As is known, metal wire is often braided when used as such a covering due to the rigidity of the metal material and/or lead flexibility requirements. Consequently, the wire density is generally limited. As exemplified from FIG. 6, typical coverage of the lead surface using such metal wire ranges from about 50% to about 75%. Such deficiency in coverage generally leads to disruption to the shield integrity and reduction of the electromagnetic reflection, thereby increasing penetration of the electromagnetic radiation through the metal wire shield and into the lead. In contrast, carbon that is formed to be continuous, e.g., carbon fiber, whether being micro-sized or nano-sized, is formed as a bundle of individual strands. As should be appreciated, these strands of the carbon fiber, when the carbon fiber is applied around the lead as described above and shown with respect to FIGS. 5A and 5B, provide for enhanced coverage—nearly 100% coverage—of the lead surface. In turn, continuous carbon fiber is found to enhance shield conductance, and in turn, shield effectiveness.

Figure 7:
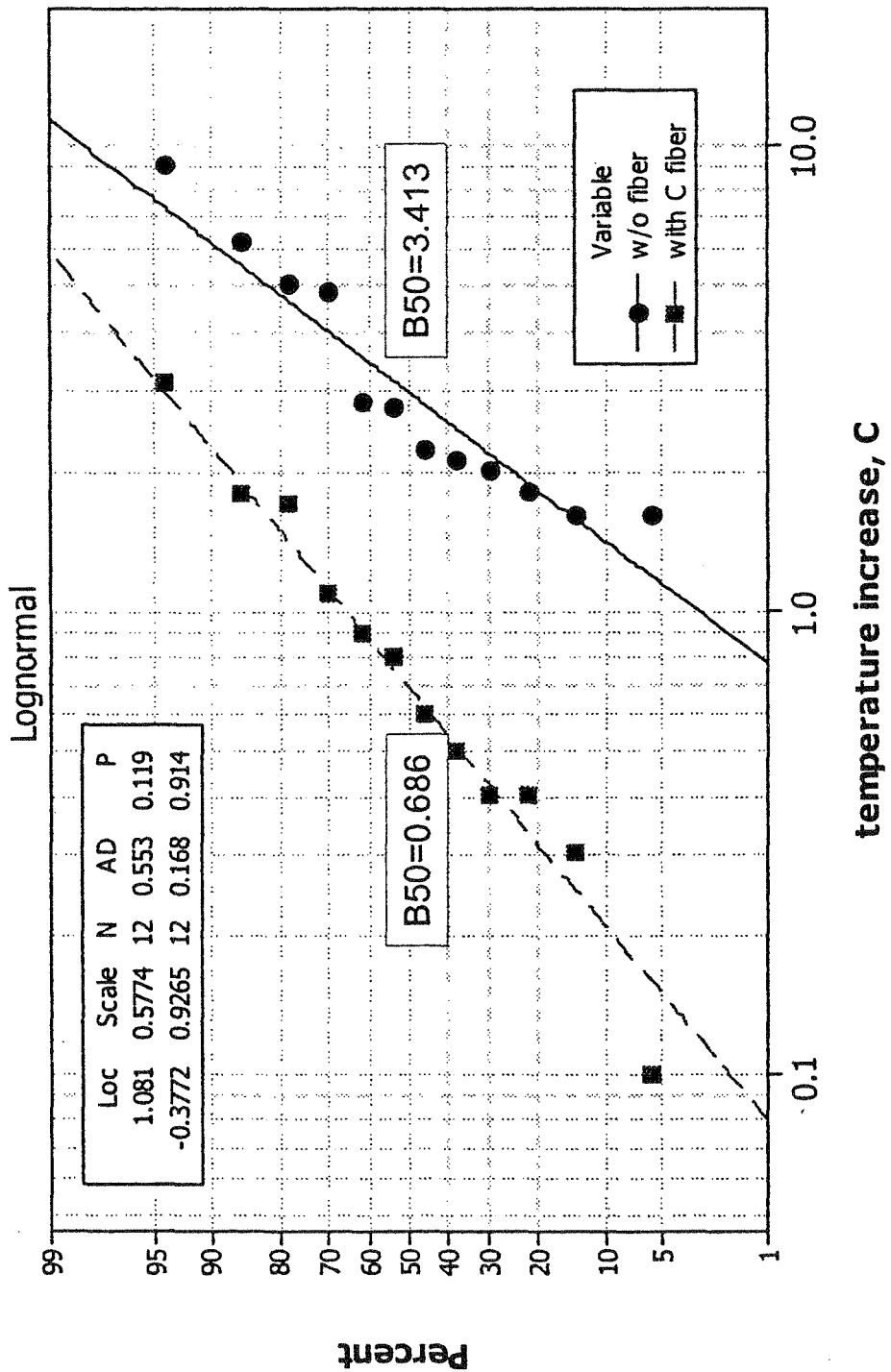
FIG. 7 is a lognormal probability plot of temperature increase in conducting leads with and without a carbon fiber shield.

Referring to FIG. 7, the effectiveness of a carbon fiber shield (as exemplarily embodied with respect to FIG. 5A) is illustrated. FIG. 7 depicts a lognormal probability plot of temperature increase in conducting leads with and without a carbon fiber shield. The lead tested was a Quad® lead, commercially available from Medtronic, Inc., located in Minneapolis, Minn., U.S.A. The lead was placed under a magnetic resonance imaging (MRI) scanner for 80 seconds with temperatures being measured on four electrodes on the lead both before and after the lead was wrapped with carbon fiber, with the measurements being repeated three times. As shown, the temperature increase data for the lead wrapped with carbon fiber shows a fairly linear lognormal distribution. In addition, the plot shows that the median of temperature increase of the carbon fiber wrapped lead is almost five times lower than that of the lead without carbon fiber. Thus, the plot illustrates the effectiveness of the carbon fiber being used as an electromagnetic radiation shielding material, while also showing temperature increase to be more linearly distributed (in log scale) than what is generally experienced from a lead without such shielding.

As described above, in certain embodiments, to further enhance the conductivity of the shield coverings 74a and 74b, the continuous material forming the coverings 74a and 74b can be provided with a metal coating. The metal coating, as described and embodied above, can be provided on the material prior to the material being wrapped or woven around the electrical lead, as shown in FIGS. 5A and 5B, respectively.

Each of FIGS. 8A-10B shows a cross-sectional view of an implantable lead having a plurality of shielding coverings in accordance with certain embodiments of the invention. Each of the implantable leads/extensions of FIGS. 8A and 8B, 9A and 9B, and 10A and 10B include the insulating layers 72 and the coverings 74a and 74b, respectively, previously described and shown respectively in FIGS. 5A and 5B. Further, each of the leads/extensions of FIGS. 5A and 8B, 9A and 9B, and 10A and 10B include one or more additional layers located proximate or adjacent to the coverings 74a and 74b. While each of the insulating layers 72, the coverings 74a and 74b, and the one or more additional layers are shown to have similar thicknesses in FIGS. 8A-10B, such is done to merely show the proper position of the layers with respect to one another. As such, the invention should not be limited by the thickness of the layers represented in FIGS. 8A-10B.

Figure 8B:
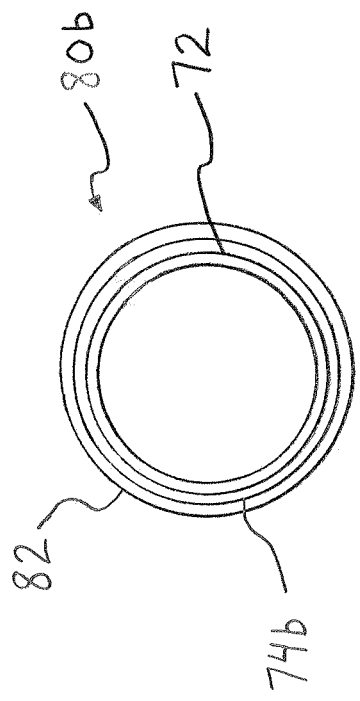
FIG. 8B is a cross-sectional view of an implantable lead/extension having a plurality of shield coverings, including those of FIG. 6B, in accordance with certain embodiments of the invention.
Figure 8A:
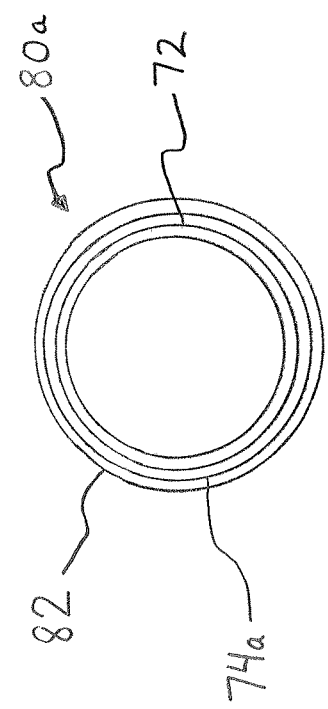
FIG. 8A is a cross-sectional view of an implantable lead/extension having a plurality of shield coverings, including those of FIG. 6A, in accordance with certain embodiments of the invention.

FIGS. 8A and 8B illustrate leads/extensions 80a and 80b, respectively. In certain embodiments, as shown, a coating 82 lies external to the coverings 74a and 74b. In certain embodiments, the coating 82 comprises one or more metals. As such, the coating 82 is adapted to enhance the shielding effect of the leads/extensions 80a and 80b. In certain embodiments, for example, the one or more metals can include Ag, Au, Cu, Co, Ni, Pt, Sn, Ta, Ti, Zn, or any alloys thereof; however, the invention should not be limited to such. Instead, the one or more metals can include any metal or combination of metals which can be used in conjunction with the coverings 74a and 74b to enhance the shielding effect of the leads/extensions 80a and 80b. In certain embodiments, the coating 82 may be applied to the coverings 74a and 74b prior to their being placed around the leads/extensions 80a and 80b, respectively. In turn, the entire outer surface area of the continuous fiber, which forms the coverings 74a and 74b, would be coated. As such, in the case of lead/extension 80a, the coating 82 would lie external and internal to the covering 74a as well as between individual fiber turns of the covering 74a. Similarly, in the case of lead/extension 80b, the coating 82 would again lie external and internal to the covering 80b; however, since the fiber of the covering 74b is woven, the coating 82 would also lie between overlapping fiber turns of the covering 80b. In certain embodiments, if the coating 82 is to be kept thin, the coating 82 may be applied to the coverings 74a and 74b via sputtering, as described in the '509 application, or by any other suitable application method.

Figure 9B:
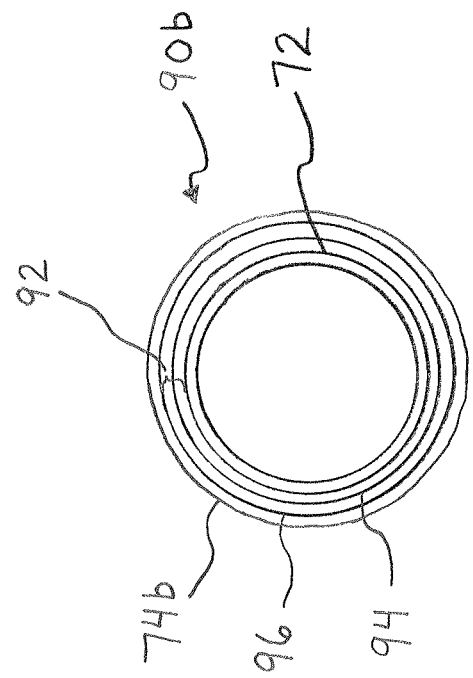
FIG. 9B is a cross-sectional view of an implantable lead/extension having a plurality of shield coverings, including those of FIG. 6B, in accordance with certain embodiments of the invention.
Figure 9A:
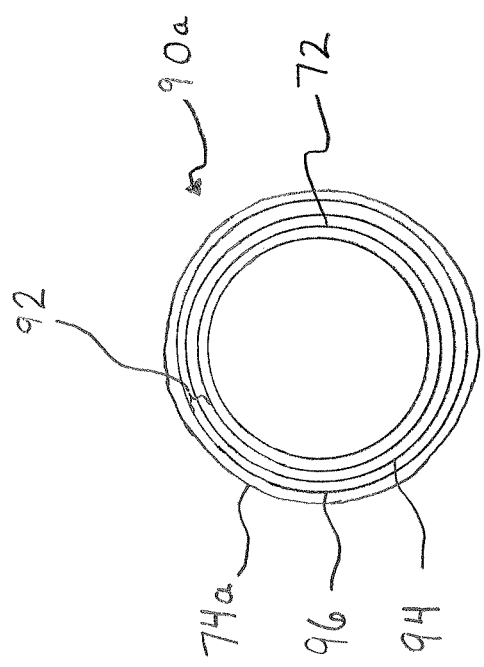
FIG. 9A is a cross-sectional view of an implantable lead/extension having a plurality of shield coverings, including those of FIG. 6A, in accordance with certain embodiments of the invention.

FIGS. 9A and 9B illustrate leads/extensions 90a and 90b, respectively. In certain embodiments, as shown, additional layers 92 lie internal to the coverings 74a and 74b; however, the invention should not so limited, as the additional layers 92, while not shown as such, can alternatively lie external to the coverings 74a and 74b just as well. In certain embodiments, the layers 92 are formed of a braided metal sheath or mesh 94 with an optional outer insulation layer 96. As such, the additional layers 92 are adapted to enhance the shielding effect of the leads/extensions 90a and 90b. In addition, the layers 92 are useful for increasing the torsional stiffness of the conductor assembly, thereby aiding the insertion of the leads/extensions 90a and 90b within the patient. In certain embodiments, the braided metal sheath or mesh 94 can be formed of Ni, Ta, Ti, or superalloy MP35N; however, the invention should not be limited to such. Instead, the metal sheath or mesh 94 can include any metal or combination of metals or alloys which can be used to enhance the shielding effect of the leads/extensions 90a and 90b. When used, the outer insulation layer 96 can be formed of silicone, a biocompatible polymer such as polyurethane, or any suitable biocompatible, non-conducting material known in the art.

Figure 10A:
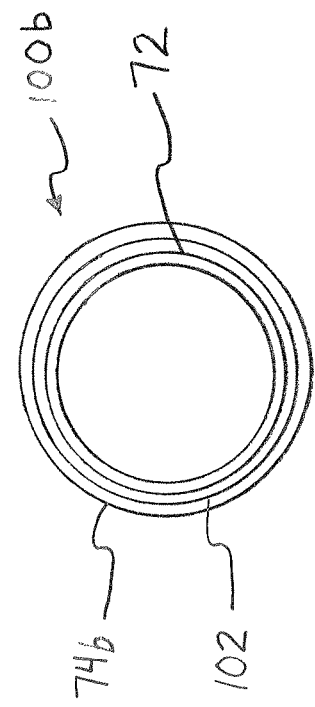
FIG. 10A is a cross-sectional view of an implantable lead/extension having a plurality of shield coverings, including those of FIG. 6A, in accordance with certain embodiments of the invention.
Figure 10B:
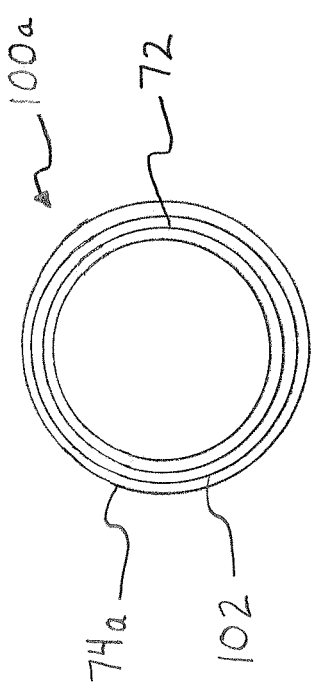
FIG. 10B is a cross-sectional view of an implantable lead/extension having a plurality of shield coverings, including those of FIG. 6B, in accordance with certain embodiments of the invention.

FIGS. 10A and 10B illustrate leads/extensions 100a and 100b, respectively. In certain embodiments, as shown, a further layer 102 lies internal to the coverings 74a and 74b. In certain embodiments, the layer 102 is formed with one or more composite materials. From the composite materials, the layer 102 is adapted to enhance the shielding effect of the leads/extensions 100a and 100b. While the layer 102 is shown to be internal to the coverings 74a and 74b, the invention should not be limited to such, as the layer 102 could just as well be switched in position with the coverings 74a and 74b (so that the further layer 102 lies external to the coverings 74a and 74b) so as to still enhance the shielding effect of the leads/extensions 100a and 100b.

As known in the art, one or more conductive materials can be combined with a polymer to create a composite with conductive properties. For the same reasons already described herein, conventional metal wire would likely not be desirable for such conductive material because it is generally limited to large sizes. As such, in certain embodiments, nano-sized metal structures and/or nano-sized non-metallic conductive structures can be provided as the conductive materials. With respect to the nano-sized non-metallic conductive structures, the structures can each have a thin metal coating so as to prevent them from clumping and further enhance their conductivity, thereby enhancing the shielding effectiveness of the composite. In certain embodiments, the conductive materials are combined with a polymeric resin, which may be selected from any of a wide variety of thermoplastic resins and elastomers, blends of thermoplastic resins, and/or thermoset resins. For example, an elastomer may be selected, e.g., silicone, polyurethane etc., which is combined with the conductive materials to form the composite, which is then deposited around the leads/extensions 100a and 100b in FIGS. 9A and 9B (or around the coverings 74a and 74b if positioned external to the coverings 74a and 74b). Those skilled in the art would recognize that the composite can comprise any of a wide variety of polymers, and is not limited to any specific elastomer.

In certain embodiments, the conductive materials involve continuous fillers, discontinuous fillers, or a combination of both. In certain embodiments, carbon, as previously described herein, either in discontinuous form or continuous form, can be correspondingly used in providing such fillers. Useful carbon discontinuous materials for the composite can include, for example, particulates, powders, fibers, filaments, flakes, and the like. In certain embodiments, the carbon discontinuous materials involve nano-sized carbon, and preferably, one or more of carbon nanofibers, carbon nanotubes, and carbon nanoflakes. Such nano-sized carbon is useful because they exhibit smaller sizes than micro-sized carbon, e.g., carbon fibers. Specifically, the smaller diameter of nano-sized carbon, e.g., carbon nanofibers, can allow for a greater percentage of cross-sectional area to be used for conducting purposes, enabling greater efficiency. Certain factors may be used for selecting one nano-sized carbon over another. For example, carbon nanotubes are relatively costly to produce, even on a commercial scale. In contrast, carbon nanofibers have relatively lower production costs than carbon nanotubes. As described above, in certain embodiments, the nano-sized carbon is provided with a metal coating. In certain embodiments, the conductive materials can include discontinuous fillers, where the fillers include one or more nano-sized metal structures. For example, the nano-sized metal structures can include particles and/or flakes, and can be formed of metals including but not limited to Ag, Au, Cu, Co, Ni, Pt, Sn, Ta, Ti, Zn, or any alloys thereof. In providing the discontinuous fillers, the nano-sized metal particles can be used alone or in combination with fillers formed of nano-sized carbon.

Such composite materials and embodiments in which the materials are used in composites for medical device lead shielding are taught in more detail in the U.S. patent application entitled "Discontinuous Conductive Filler Polymer-Matrix Composites for Electromagnetic Shielding", which is filed concurrently herewith and incorporated herein in its entirety.

In certain embodiments, the leads/extensions 100a and 100b of FIGS. 10A and 10B may further contain one or more of the coating 82 of FIGS. 8A and 8B and the additional layers 92 of FIGS. 9A and 9B to further enhance the shielding effect of the leads/extensions 100a and 100b. If the coating 82 is included on the leads/extensions 100a and 100b, in certain embodiments, the coating 82 can lie external to one or more of the coverings 74a and 74b and the carbon composite material layer 102. If the additional layers 92 are included on the leads/extensions 100a and 100b, in certain embodiments, the additional layers 92 can lie internal or external to the coverings 74a and 74b, and internal or external to the carbon composite material layer 102.

It will be appreciated the embodiments of the present invention can take many forms. The true essence and spirit of these embodiments of the invention are defined in the appended claims, and it is not intended the embodiment of the invention presented herein should limit the scope thereof.

What is claimed is:

1. An apparatus for alleviating the adverse effects of various health ailments of a patient comprising:
 a medical device; and
 an electrical lead connected to the medical device at a proximal end of the lead and having at least a distal end, the distal end of the electrical lead having one or more electrodes or electrical contacts for sensing and/or therapy delivery, the electrical lead comprising a conductor assembly having one or more conductors covered by an insulating layer and the electrical lead further comprising a shield covering adjacent in a radial direction or proximate in the radial direction to at least a portion of the insulating layer to shield the conductors from one or more electromagnetic fields, the shield covering comprising carbon or coated carbon fibers, the carbon or coated carbon fibers forming a material that is in a wrapped or woven form so as to form a layer of the shield covering having multiple turns of the material where each turn of the material forming the layer wraps completely around the insulating layer and contacts another turn of the material that is adjacent in an axial direction of the lead and where the contact between adjacent turns of the material occurs over the entire circumference of each turn, the carbon or coated carbon fibers having an effective combination of small size and high surface area for sufficient conductivity in presence of one or more high frequency electromagnetic fields so that interference to the operation of the one or more conductors is minimized.

2. The apparatus of claim 1, wherein the carbon is formed of one or more of carbon fiber, carbon nanofiber, and carbon nanotube having one or more of single and multiple walls.

3. The apparatus of claim 1, wherein the carbon has one or more conductive members each having an outer diameter that is no greater than about 20 μm.

4. The apparatus of claim 1, wherein the carbon has a higher skin depth than metal.

5. The apparatus of claim 1, wherein the coated carbon fibers have a coating formed of one or more metals, the coating formed or attached around the carbon, the coating and the shield covering providing an enhanced shielding effect for the one or more conductors.

6. The apparatus of claim 1, wherein the medical device is an implantable medical device, the device and the electrical lead being implanted within the patient.

7. The apparatus of claim 1, wherein the electrical lead further includes a lead extension electrically connecting the lead to the medical device, the shield covering positioned adjacent or proximate to at least a portion of the lead extension.

8. The apparatus of claim 1, wherein the multiple turns do not overlap.

9. The apparatus of claim 1, wherein the multiple turns do overlap.

10. An apparatus for alleviating the adverse effects of various health ailments of a patient comprising:
   a medical device; and
   an electrical lead connected to the medical device at a proximal end of the lead and having at least a distal end, the distal end of the electrical lead having one or more electrodes or electrical contacts for sensing and/or therapy delivery, the electrical lead comprising:
      a conductor assembly having one or more conductors covered by an insulating layer,
      a shield covering adjacent in a radial direction or proximate in the radial direction to at least a portion of the insulating layer to shield the conductors from one or more electromagnetic fields, the shield covering formed of carbon, the carbon forming a material that is in a wrapped or woven form so as to form a layer of the shield covering having multiple turns of the material where each turn of the material forming the layer wraps completely around the insulating layer and contacts another turn of the material that is adjacent in an axial direction of the lead and where the contact between adjacent turns of the material occurs over the entire circumference of each turn, and
      a conductive layer immediately adjacent the shield covering that encircles the conductor assembly.

11. The apparatus of claim 10, wherein the conductive layer is a metal coating exterior to the shield covering.

12. The apparatus of claim 10, further comprising a metal braid or sheath interior to the shield covering.

13. An apparatus for alleviating the adverse effects of various health ailments of a patient comprising:
   a medical device; and
   an electrical lead connected to the medical device at a proximal end of the lead and having at least a distal end, the distal end of the electrical lead having one or more electrodes or electrical contacts for sensing and/or therapy delivery, the electrical lead comprising a conductor assembly having one or more conductors covered by an insulating layer and a shield covering adjacent in a radial direction or proximate in the radial direction to at least a portion of the insulating layer to shield the conductors from one or more electromagnetic fields, the shield covering formed of carbon that encircles the conductor assembly, the carbon forming a material that is in a wrapped or woven form so as to form a layer of the shield covering having multiple turns of the material where each turn of the material forming the layer wraps completely around the insulating layer and contacts another turn of the material that is adjacent in an axial direction of the lead and where the contact between adjacent turns of the material occurs over the entire circumference of each turn, the carbon having an effective combination of small size and high surface area for sufficient conductivity in presence of one or more high frequency electromagnetic fields so that interference to the operation of the one or more conductors is minimized.

* * * * *